US011344517B2

(12) United States Patent
Mitidieri et al.

(10) Patent No.: US 11,344,517 B2
(45) Date of Patent: *May 31, 2022

(54) INJECTABLE SUPERSATURATED ACETAMINOPHEN SOLUTION FOR SPINAL ADMINISTRATION

(71) Applicant: Sintetica S.A., Mendrisio (CH)

(72) Inventors: Augusto Mitidieri, Morcote (CH); Elisabetta Donati, Cavallasca (IT); Nicola Caronzolo, Bissone (CH)

(73) Assignee: SINTETICA S.A., Mendrisio (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/411,532

(22) PCT Filed: Jun. 27, 2013

(86) PCT No.: PCT/IB2013/055277
§ 371 (c)(1),
(2) Date: Dec. 29, 2014

(87) PCT Pub. No.: WO2014/002042
PCT Pub. Date: Jan. 3, 2014

(65) Prior Publication Data
US 2015/0148379 A1 May 28, 2015

(30) Foreign Application Priority Data
Jun. 29, 2012 (IT) .......................... MI2012A001154

(51) Int. Cl.
A61K 31/167 (2006.01)
A61K 31/245 (2006.01)
A61K 9/00 (2006.01)
A61K 31/445 (2006.01)
A61K 31/381 (2006.01)
A61K 31/47 (2006.01)
A61K 9/08 (2006.01)

(52) U.S. Cl.
CPC .......... A61K 31/167 (2013.01); A61K 9/0085 (2013.01); A61K 9/08 (2013.01); A61K 31/245 (2013.01); A61K 31/381 (2013.01); A61K 31/445 (2013.01); A61K 31/47 (2013.01)

(58) Field of Classification Search
CPC .. A61K 31/167; A61K 9/0085; A61K 31/245; A61K 31/445
See application file for complete search history.

(56) References Cited

U.S. PATENT DOCUMENTS 5,766,321 A * 6/1998 Ishihara .................. C02F 1/20
  96/202
6,028,222 A   2/2000 Dietlin et al.
6,171,298 B1 * 1/2001 Matsuura .............. A61L 17/145
  604/891.1
6,992,218 B2   1/2006 Dietlin et al.
2004/0054012 A1   3/2004 Dietlin et al.
2005/0203175 A1 * 9/2005 Tseti ...................... A61K 47/22
  514/474
2006/0084703 A1   4/2006 Nguyen-Xuan
2009/0143474 A1 * 6/2009 Royal et al. .................. 514/629
2011/0015273 A1   1/2011 Kandhagatla et al.
2012/0035267 A1   2/2012 Dasberg et al.

FOREIGN PATENT DOCUMENTS

EP        1752139        2/2007
IN        200801746    *  8/2008
WO    WO 2002/072080    *  9/2002
WO    2004071502 A1      8/2004
WO    2009143558 A1     12/2009
WO    2012001494         1/2012

OTHER PUBLICATIONS

Wikipedia, Paracetamol, (Feb. 6, 2011), pp. 1-7.*
WO 2002/072080 machine translation, Eschenbach, Bernd et al., (Sep. 2002), pp. 1-6.*
drugs.com, Paracetamol, Dec. 7, 2009, pp. 1-4.*
Granberg, et al., "Solubility of Paracetamol in Pure Solvents" Journal of Chemical & Engineering Data, vol. 44, No. 6, Nov. 1, 1999.
Pelissier et al., "Paracetamol Exerts a Spinal Antinociceptive Effect Involving an Indirect Interaction with 5-Hydroxytrytptamine3 Receptors: In Vivo and In Vitro Evidence", Journal of Pharmacology and Experimental Therapeutics, American Society for Pharmacology and Experimental Therapeutics, U.S. vol. 278, No. 1, Jul. 1, 1996.
International Search Report of PCT/IB2013/055277 dated Nov. 11, 2013.
International Preliminary Report on Patentability of PCT/IB2013/055277 dated Sep. 17, 2014.
Office Action dated May 28, 2015 in the counterpart Peruvian patent application, including a brief English Translation.
English translation of an office Action issued by the Colombian Patent Office in a counterpart application.
Letter reporting office action issued by the Colombian patent office in a counterpart application.
Office Action issued by the Colombian patent office in a counterpart application.
English Translation of office action issued in counterpart Colombian patent application 15-015754 dated Oct. 21, 2016.
Frey K, et al., "The Recovery Profile of Hyperbaric Spinal Anesthesia With Lidocaine, Tetracaine, and Bupivacaine," Regional Anesthesia and Pain Medicine, 23(2): 159-163, 1998.
Jensen FM, et al., "Direct spinal effect of intrathecal acetaminophen on visceral noxious stimulation in rabbits," Acta Anaesthesiol Scand, Nov. 1992;36(8):837-41.

(Continued)

Primary Examiner — Andrew S Rosenthal
Assistant Examiner — Lyndsey M Beckhardt
(74) Attorney, Agent, or Firm — Troutman Pepper Hamilton Sanders LLP (Rochester)

(57) ABSTRACT

The present invention relates to an acetaminophen injectable aqueous solution for use in the treatment or in the prevention of pain by spinal administration, wherein said acetaminophen injectable solution is supersaturated. In certain embodiments, the acetaminophen injectable aqueous solution is administered simultaneously, separately or sequentially with a local anaesthetic by spinal administration.

4 Claims, 4 Drawing Sheets

(56) References Cited

OTHER PUBLICATIONS

PubChem Acetaminophen Sep. 25, 2017, p. 1.
Alloui A., et al., "Paracetamol exerts a spinal, tropisetron-reversible, antinociceptive effect in an inflammatory pain model in rats", European Journal of Pharmacology, 443 (2002) 71-77.
English translation of office Action received in counterpart Oman Patent Application dated Sep. 26, 2018.
English translation of opposition cited in counterpart Ecuadorian Application dated Nov. 6, 2018.
Furuhama K., et al., "Optimum properties of injectable test solutions for intrathecal administration to conscious rats", J.Vet. Med. Sci 59(12)4103-1107, 1997.
Huseyin S., et al., "The analgesic effect of paracetamol when added to lidocaine for intravenous regional anesthesia", Anesth Analg 2009; 109:1327-30.

* cited by examiner

INJECTABLE SUPERSATURATED ACETAMINOPHEN SOLUTION FOR SPINAL ADMINISTRATION

This application is a U.S. national stage of PCT/IB2013/055277 filed on 27 Jun. 2013, which claims priority to and the benefit of Italian Application No. MI2012A001154 filed on 29 Jun. 2012, the contents of which are incorporated herein by reference in their entirety.

FIELD OF THE INVENTION

The present invention relates to an acetaminophen injectable solution for spinal administration.

The present invention originates from the field of drugs in liquid form suitable for spinal administration.

More specifically, the present invention relates to an injectable pharmaceutical formulation containing acetaminophen as active ingredient for the treatment of post-surgical pain by spinal administration.

PRIOR ART

Acetaminophen (acetyl-p-aminophenol), commonly known as paracetamol (CAS no: 103-90-2), is an active ingredient possessing analgesic and antipyretic activity used widely in medical practice to alleviate acute and chronic pain and to reduce the body temperature when this exceeds physiological values.

Paracetamol, conversely to the majority of commonly used analgesic drugs, is not an NSAID (non-steroidal anti-inflammatory drug), since it is almost devoid of antiaggregant and anti-inflammatory activity. To date, its mechanism of action remains little known, although this molecule was synthesised for the first time in 1878 and its use in the medical field has been established for more than 100 years.

In the clinical field, acetaminophen is used fundamentally as an analgesic in the treatment of mild and medium pain and as an antipyretic in the treatment of febrile states in adults and in children.

The most common pharmaceutical form for this active ingredient is the solid form. The most typical paracetamol-based pharmaceutical formulations are those in solid tablet form, in granule form or in the form of suppositories. Moreover, formulations containing acetaminophen in the form of a solution for intravenous infusion can also be found on the market. These are formulations indicated for the short-term treatment of pain of medium intensity, in particular of the type experienced following a surgical intervention. Intravenous administration is reserved for cases in which, from a clinical viewpoint, there is the need to treat the pain and/or hyperthermia with urgency or in cases in which it is impossible to implement the other administration methods.

Administration of acetaminophen by means of methods alternative to traditional methods is still yet to be explored extensively, and essentially no specific applications have been found in the field of analgesic therapy.

Since acetaminophen is devoid of anaesthetic action, it is yet to be used in the field of general, local or locoregional anaesthesia, such as spinal anaesthesia. Spinal anaesthesia is an anaesthesia technique in which an injectable solution containing an active ingredient possessing local anaesthetic activity is injected through the dura mater, that is to say the outer meningeal membrane protecting the spinal cord, into the medullary canal thereof. The spinal injection is usually carried out by highly qualified medical personnel between the spinous processes of two vertebrae, usually in the lumbar zone, using specific needles, which are long and slender.

The solution containing the active ingredient possessing local anaesthetic activity, once injected in situ, mixes with the cerebrospinal fluid, that is to say the biological fluid that bathes the spinal cord and is located between the spinal cord and the dura. During the spinal injection, the risks of causing neurological damage are limited by the fact that the spinal column is protected by the pia mater, the innermost of the meningeal membranes.

During the infusion process, the solution containing the local anaesthetic mixes with the cerebrospinal fluid, thus blocking conduction via the nervous system of impulses to the brain and causing a reversible loss of sensitivity, which may be accompanied by motor paralysis. The anaesthesia is thus implemented both from the anterior part of the spinal cord, from which the motor nerves originate, and from the posterior part, from which the sensory nerves enter. The administration of the solution containing the anaesthetic then causes the absence of sensitivity of the innervated areas from the nerve roots in question, and at the same time the inhibition of muscular and sensory activity.

Generally, spinal anaesthesia is used for interventions on organs of the small pelvis and on the lower limbs. Typical examples where spinal anaesthesia is used are appendectomy, hernioplasty, caesarean section, arthroscopy, orthopaedic surgery of the lower limbs, etc.

Among the spinal anaesthesia techniques, it has been possible to distinguish between epidural injection and intrathecal (IT) injection. In the latter case, the solution containing local anaesthetic is injected into what is known as the subarachnoid space.

Whereas the intrathecal technique is more invasive than the epidural technique since the injection is performed in a deeper zone of the spine, it has the advantage of requiring comparably lower doses of local anaesthetic. This aspect generally constitutes an advantage since local anaesthetics have a certain neurotoxicity.

Depending on the local anaesthetic used, the spinal anaesthesia can last from one to three hours approximately. Once this action ceases, the patient progressively regains mobility and sensitivity; the perception of pain increases as time passes due to the effects of the surgical procedure.

The analgesic action of local anaesthetics therefore fundamentally remains limited to the period of the surgical intervention, for which reason it is essential to establish suitable analgesic therapy in the immediate post-surgical period. In the first hours following the surgical intervention, the sensation of generalised pain is localised in the region of the wound and is in fact particularly intense, and it is therefore necessary to establish an effective and prompt analgesic therapy.

In medical practice, it has been observed however that, in order to obtain a suitable post-surgical analgesic effect, it is necessary to administer analgesics in high quantities or, alternatively, to resort to the administration of opioid drugs.

Both of these therapeutic approaches not only expose patients to a series of possible side effects varying in accordance with the type and quantity of drug administered, but also, in many cases, do not provide a suitable analgesic response.

Currently, there is therefore a need to provide new analgesic therapies to be matched with local or locoregional anaesthesia in order to provide an effective analgesic action when the local anaesthetic effect reduces or stops.

One of the objects of the present invention is therefore to provide pharmaceutical formulations for spinal administration that make it possible to obtain an effective analgesic action in cases of acute post-surgical pain.

Another object of the present invention is to provide an injectable solution containing an analgesic active ingredient suitable for spinal administration in the event of locoregional anaesthesia, said solution having an effective and durable analgesic action on the patient when the action of the local anaesthetic runs out.

SUMMARY OF THE INVENTION

The inventors of the present patent application have now found that by administering a supersaturated aqueous solution of acetaminophen by spinal route, a prolonging of the analgesic effect substantially devoid of side effects, is surprisingly obtained.

In accordance with a first aspect, the present invention provides an acetaminophen supersaturated injectable aqueous solution for analgesic use by spinal administration, wherein said supersaturated injectable aqueous solution comprises acetaminophen in a concentration ranging from 1.3 to 8% w/v.

The acetaminophen supersaturated aqueous solutions according to the invention with a concentration from 1.3 to 8% w/v are unexpectedly stable, even after a period of storage of more than 18 months.

The inventors have discovered that, by means of spinal administration of an acetaminophen supersaturated injectable aqueous solution, it is possible to obtain an effective analgesic effect of unexpectedly prolonged duration, typically equal to or greater than 24 hours. In particular, the spinal administration of an acetaminophen supersaturated solution according to the invention results in effective analgesia for at least 24 hours in mice and in rats in the case of inflammatory pain induced by carrageenan and in post-surgical pain.

The inventors have also found that acetaminophen supersaturated aqueous solutions are compatible with conventional solutions of local anaesthetics and can therefore be co-administered by spinal administration. Co-administration with local anaesthetics is made possible or is facilitated in any case since the solutions according to the invention have a quantity of solvent less than that of unsaturated acetaminophen solutions.

The administration of injectable solutions by spinal administration generally presents limitations. A first limitation is of the physical type, since, in the case of spinal anaesthesia, the drug is perfused in a defined and confined space in which a limited quantity of solution can be infused. In the case of the acetaminophen hypersaturated solution, this limitation is overcome since a therapeutically effective quantity of active ingredient is dissolved in a volume of solvent that is reduced compared to an unsaturated conventional solution of the same active ingredient.

The low volume of supersaturated solution needed to obtain an analgesic therapeutic response allows the simultaneous administration with local anaesthetic solutions.

For example, an acetaminophen supersaturated solution with a volume of approximately 0.5-1.5 ml of water can be added to a solution of equal volume of local anaesthetic in order to obtain a total solution of approximately 1-6 ml that can be administered by means of spinal administration without exceeding the physiological limits imposed by the subdural space (intrathecal).

The acetaminophen supersaturated solution can therefore be added to and/or mixed with a conventional solution of a local anaesthetic in order to obtain effective analgesia for a period of time greater than the period of activity of the anaesthetic, in particular in the case in which the anaesthetic is a short-acting or medium-acting anaesthetic.

In addition, the acetaminophen solutions and the local anaesthetic solutions have increased chemical-physical compatibility, which allows these solutions to be used concomitantly or in mixture.

In accordance with a second aspect of the invention, an acetaminophen supersaturated aqueous solution is provided for analgesic use, comprising its simultaneous, separate or sequential spinal administration with a local anaesthetic.

The simultaneous, separate or sequential spinal administration of an acetaminophen supersaturated aqueous solution with a local anaesthetic is also made possible due to the increased stability of the acetaminophen supersaturated aqueous solution as such or in mixture with conventional local anaesthetics.

In some embodiments, spinal administration of the acetaminophen supersaturated solution is implemented before pain is perceived, typically before a surgical intervention. The analgesic action determined by the acetaminophen has a positive additive effect, and not a synergistic effect, with respect to the anaesthesia produced by the local anaesthetic. The duration of the sensory and motor block remains unchanged. The pharmacokinetics of the anaesthetic thus remains unchanged, enabling rapid discharge of the patient in the case of joint administration with short-acting anaesthetics in clinical practice.

In accordance with a third aspect of the invention, a process for preparing an acetaminophen supersaturated aqueous solution, in particular of the type described above, is provided.

With the process for preparing the acetaminophen supersaturated aqueous solution according to the invention, the presence of oxygen or of dissolved air in the solvent is typically eliminated or substantially reduced, thus causing an increase of the stability of the acetaminophen solution.

In accordance with this aspect of the invention, a process for preparing an acetaminophen supersaturated solution comprising the dissolution of acetaminophen in a deoxygenated-water-based solvent, for example by degassing with a flow of inert gas, typically nitrogen and/or an inert gas, for example argon.

The acetaminophen supersaturated solution obtained with the process according to the invention is highly stable, has an increased concentration of acetaminophen in the solvent, and can be mixed with a solution of a conventional local anaesthetic in order to obtain a solution with a total volume that is compatible with the volume injectable by means of spinal administration in a single administration process.

In accordance with a further aspect of the invention, a method for treating pain, in particular acute post-surgical pain, comprising spinal infusion of an acetaminophen supersaturated injectable aqueous solution having a concentration from 1.3 to 8% w/v in a therapeutically effective amount is provided. Spinal administration of acetaminophen supersaturated solution can be implemented simultaneously, separately or sequentially with the administration of a local anaesthetic.

In some embodiments, the analgesic treatment method according to the invention comprises the administration of a therapeutically effective quantity of acetaminophen supersaturated solution before pain is perceived, typically before the surgical intervention. In these conditions, the analgesic effect achieved has an unexpectedly prolonged duration, for example greater than 24 hours.

DETAILED DESCRIPTION OF THE INVENTION

Figure 1:
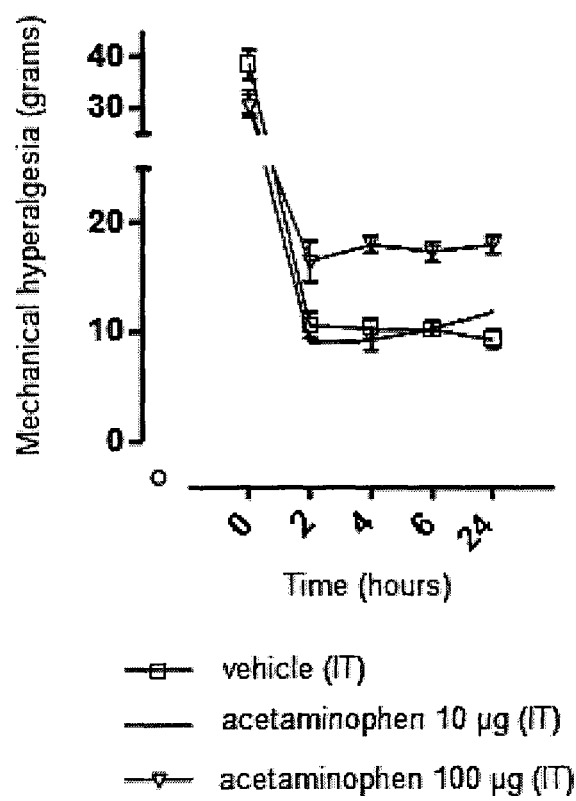
FIG. 1 shows a graph illustrating the analgesic effect over time of two solutions containing, respectively, 10 and 100 μg of acetaminophen in hyperalgesia caused by induction of peripheral inflammation.

In accordance with a first aspect, the invention relates to an acetaminophen injectable aqueous solution for analgesic use by spinal administration, wherein said injectable solution is supersaturated and conveniently comprises acetaminophen dissolved in water in a concentration ranging from 1.3 to 8% w/v.

In accordance with some embodiments, the acetaminophen injectable aqueous solution is supersaturated and has a concentration ranging from 1.8 to 8.0 w/v of acetaminophen.

In accordance with some embodiments, the acetaminophen injectable aqueous solution is supersaturated and has a concentration ranging from 1.3 to 2.3% w/v.

The applicant has found that the use of acetaminophen supersaturated solutions makes it possible to reduce the volume of solvent to be administered in the intrathecal space, thus enabling the co-administration with injectable solutions of conventional local anaesthetics.

Solutions of acetaminophen with concentrations equal to or greater than 1.3% can be used within the scope of the invention. These injectable solutions provide good compliance and manageability of use.

In certain embodiments, the acetaminophen supersaturated solution has a concentration of 1.3 to 8% w/v, from 1.8 to 8% w/v, from 1.8 to 3% w/v, from 1.3 to 2.3% w/v.

In certain embodiments, the acetaminophen supersaturated solutions of the invention have a concentration of or greater than 1.8% w/v.

Within the scope of the invention, the acetaminophen solution is implemented so as to administer a therapeutically active quantity of active ingredient.

The term "therapeutically active" means a dose that causes a significant analgesic response in the subject to whom the acetaminophen supersaturated solution is administered. This dose varies according to the conditions, age and weight of the patient.

In accordance with some embodiments, the analgesic effect caused by acetaminophen has a positive additive action, and not a synergistic action, with respect to the anaesthesia produced by the local anaesthetic. The duration of the sensory and motor block remains unchanged. The pharmacokinetics of the anaesthetic thus remains unchanged, enabling a rapid discharge of the patient in the case of joint administration with short-acting anaesthetics in human clinical practice.

Within the scope of the invention, the term "saturated solution" means a solution that has dissolved therein the maximum quantity of solute possible at a specific temperature, typically set at 20° C.

The term "supersaturated" solution means a solution that has a concentration of solute greater than the one that could be dissolved in water, in particular distilled water for pharmaceutical use, at a temperature of 20° C.

Typically, in the supersaturated solution according to the invention, acetaminophen represents the solute in excess that does not separate spontaneously by crystallisation. This is a "hysteresis" phenomenon widely recognised in physics and caused by a "conflict" between contrasting factors, some of which attempt to draw the phenomenon in one direction (for example thermodynamics, which would promote crystallisation of the solute in excess), and others of which are instead obstructive (for example the viscosity of the solution and above all the absence of enucleation centres that enable crystallisation, these all being factors that delay the crystallisation process).

Specifically, within the scope of the invention, the term "acetaminophen supersaturated solution" means solutions with a concentration of acetaminophen equal to or greater than approximately 13 mg/ml or 1.3% w/v in water, at a temperature of 20° C.

The term "acetaminophen dose" means a quantity of acetaminophen and/or salts or derivatives thereof that can effectively cause central locoregional anaesthesia following perfusion via spinal administration.

The acetaminophen supersaturated solution may have a concentration of acetaminophen no greater than 100 mg/ml, corresponding to 10% w/v, beyond which recrystallisation of the active ingredient may occur.

Typically, the acetaminophen supersaturated solutions according to the invention have an acetaminophen concentration ranging from 1.3 to 2.3%.

In the acetaminophen supersaturated solution according to the invention, the solvent phase is water-based, typically sterile and apyrogenic.

In accordance with some embodiments, the acetaminophen supersaturated solution is substantially free of preservatives, and/or additives and/or co-solvents.

In accordance with some embodiments, the supersaturated solution according to the invention has a pH ranging from 4.5 to 6.5. In some embodiments, this pH range is regulated by adding a buffering agent in suitable quantities.

In accordance with some embodiments, the acetaminophen solution according to the invention has a pH substantially equal to 5.5.

In accordance with some embodiments of the invention, the acetaminophen supersaturated solution according to the invention comprises one or more buffering agents.

In order to regulate the pH of the solution according to the invention in a predetermined range, it is possible to use any buffering agent used in the formulation of solutions injectable by spinal administration. By way of example, suitable buffering agents comprise carboxylic acids, such as citric acid, or alkaline or earth alkaline phosphates or biphosphates, such as sodium dihydrogen phosphate ($Na_2HPO_4$).

In accordance with some embodiments, the acetaminophen solution according to the invention has an osmolality ranging between 80 and 310 mOsm/kg. In order to modify the osmolality of the solution itself, it is possible to use isoosmotic agents.

In some embodiments, the acetaminophen solution according to the invention has a relative density at 20° C. ranging between 1.003 and 1.075 g/g.

Typically, the acetaminophen supersaturated aqueous solution according to the invention is used in the treatment and/or in the prevention of pain and in particular in post-surgical analgesic treatment. By way of example, the acetaminophen supersaturated solution is used in the post-surgical analgesic therapy of surgical interventions such as appendectomy, hernioplasty, caesarean section, arthroscopy, orthopaedic surgery of the lower limbs, etc.

In some embodiments, in order to obtain an effective analgesic effect, a quantity of acetaminophen ranging from 6 to 60 mg, typically from 8 to 40 mg, is injected by spinal administration.

By way of example, it is possible to administer an amount of supersaturated solution ranging from 0.5 to 1.3 ml containing acetaminophen at 1.8% w/v in order to obtain these therapeutic doses.

The therapeutic effect achieved as a result of spinal administration of quantities of acetaminophen considerably less than those required by other administration methods in order to obtain an equal response represents one of the advantages of the present invention.

By way of example, the effective dose of acetaminophen administered by spinal administration in the form of a supersaturated solution according to the invention is approximately $1/100$ of the dose of acetaminophen administered orally necessary to obtain the same analgesic response. In fact, in humans, the maximum oral dose permitted within 24 hours is equal to 4 g. The maximum spinal dose envisaged for human clinical practice is equal to 40 mg, this being a dose that can also be used in patients with hepatic pathologies.

This drastic reduction of the dosage of active ingredient necessary to obtain an analgesic response comprises a series of advantages in terms of reduction of systemic toxicity of the drug and of side effects. In particular, the low dosages of acetaminophen necessary to obtain an analgesic effect by spinal administration of the formulation according to the invention considerably reduce the risks of hepatotoxicity associated with the administration of acetaminophen.

In addition, the low volume of acetaminophen supersaturated solution needed to obtain a suitable therapeutic response allows said solution to be mixed or administered simultaneously with other active ingredients in the form of a solution that can be injected by spinal administration, since the post-injection increase in volume of the cerebrospinal fluid returns to within physiological limits.

In accordance with some embodiments, the acetaminophen supersaturated solution is administered intrathecally.

In some embodiments, the acetaminophen supersaturated solution according to the invention has a content of air or oxygen dissolved in the water solvent of less than 200 ppb.

The considerable absence of oxygen increases the stability of the acetaminophen solution according to the invention, making it possible to store it for long periods of time, up to more than 18 months. The stability has also been confirmed at low and high temperatures by carrying out studies at 4° C., 40° C. and 60° C., and the solutions demonstrated themselves to be stable for at least 3, 6 and 3 months respectively.

In some embodiments, the acetaminophen supersaturated solution contains deoxygenated water as solvent.

In accordance with a second aspect of the invention, a process for producing an acetaminophen supersaturated solution, comprising the solubilisation of acetaminophen in an amount greater than or equal to 13 mg/ml (1.3% w/v) in deoxygenated water by means of nitrogen flushing is provided.

In some embodiments, the process for preparing the solution according to the invention comprises the mixing of water by injection and acetaminophen in a nitrogen atmosphere or in the presence of a nitrogen stream, in which the acetaminophen is provided in an amount so as to give an acetaminophen supersaturated medicated solution.

In accordance with certain embodiments, the process for preparing an acetaminophen solution of the invention comprises an elimination step of the oxygen or a degassing step of the solvent, which typically is water.

In some embodiments, the elimination of oxygen or the degassing of the water comprises a step of treatment of water with an inert gas, typically nitrogen and/or a noble gas, for example argon.

In accordance with some embodiments, the process for producing the acetaminophen supersaturated solution comprises the following steps:
 a) dissolution of acetaminophen in deoxygenated or degassed water conveniently by the passage of a nitrogen flow,
 b) filtration of the acetaminophen solution obtained in nitrogen stream,
 c) distribution of the solution in nitrogen stream,
 d) sterilisation of the solution.

In some embodiments, step a) is carried out at a higher temperature than room temperature, for example ranging from 55 to 70° C. to produce the supersaturated solution of acetaminophen.

In accordance with some embodiments of the process, in the initial step of dissolution of acetaminophen in water, one or more buffering agents, typically citric acid and/or sodium dihydrogen phosphate, are added in order to regulate the pH of said aqueous solution, for example in the range from 4.5 to 6.5.

In accordance with some embodiments, step b) of filtration of the acetaminophen solution is carried out by means of sterilising filter. Step b) can be carried out at a higher temperature than the ambient temperature, for example ranging from 70 to 80° C.

In some embodiments, step c) of distribution is performed at a temperature greater than room temperature, for example ranging from 55 to 75° C.

In accordance with some embodiments, the step d) of sterilisation of the acetaminophen solution is carried out by means of heating, typically to temperatures greater than 100° C. for a period of time suitable for sterilisation, for example equal to or greater than 15 minutes In accordance some embodiments, the acetaminophen supersaturated solution of the invention is obtained with a process that comprises the following steps:
 a) Dissolution of acetaminophen in deoxygenated water, for example by degassing in a nitrogen stream at a higher temperature than room temperature, conveniently ranging from 55 to 70° C.
 b) Filtration of the solution in a nitrogen stream at a higher temperature than room temperature, for example ranging from 70 to 80° C.
 c) Distribution of the solution in a nitrogen stream at a higher temperature than room temperature, for example ranging from 55 to 75° C.

In accordance with some embodiments, the acetaminophen supersaturated solution is packaged in suitable sterile vials in the presence of inert gas, typically nitrogen, in order to prevent oxidative phenomena, which could compromise the stability of the solution.

In accordance with a third aspect of the present invention, an acetaminophen supersaturated aqueous solution for analgesic use comprising simultaneous, separate or sequential spinal administration with a local anaesthetic is provided.

In accordance with another aspect, the present invention provides an analgesic treatment method comprising the spinal administration of an acetaminophen supersaturated solution according to any one of the previously described embodiments.

The results of the experiments on animal models conducted by the applicant have demonstrated that the spinal administration of an aqueous solution of paracetamol, of the type previously described, determines an anti-hyperalgesic effect and anti-allodynic effect of the paracetamol in pain models such as post-operative and acute inflammatory pain resulting from the intraplantar administration of carrageenan.

Experimental data shows that in inflammatory or post-operative pain models, the administration of a paracetamol solution of the invention exerts a effective and prolonged analgesic and anti-allodynic action that is not predictable from the literature data.

In particular, under the experimental conditions in which the acetaminophen solution of the invention was tested, the activation of a neuronal firing is provoked in the affected area, where the paracetamol is effective in controlling the intensity of the ascending stimulus, decreasing the awareness and sensitivity of the algesic threshold thus determining an unexpectedly prolonged analgesic effect.

In some embodiments, the acetaminophen supersaturated solution is administered simultaneously with the administration of a local anaesthetic.

In some embodiments, the simultaneous administration requires the mixing of the acetaminophen solution with a solution of a local anaesthetic.

One of the advantages of the acetaminophen supersaturated solution is provided by the possibility of having an elevated content of active ingredient in a reduced volume of solvent. The acetaminophen solutions according to the invention typically contain from 1.3 to 2.3 mg per ml of solvent, typically water for injection.

These solutions can be mixed with the solutions of conventional local anaesthetics, which typically have a volume ranging between 1 and 2.5 ml, to obtain a final mixture for infusion with a total volume conveniently ranging from 2 to 4 ml.

The simultaneous spinal administration of local anaesthetic and acetaminophen supersaturated solution makes it possible to obtain a combined anaesthetic and analgesic effect by carrying out a single spinal injection, thus limiting the risks of injury to the spinal cord of the patient and increasing the compliance with the combined anaesthetic-analgesic treatment.

In accordance with a further aspect, the present invention provides a method of combined anaesthetic-analgesic treatment, which comprises the simultaneous, separate or sequential administration of an acetaminophen supersaturated solution and a solution of local anaesthetic.

A further advantage of the acetaminophen solution according to the invention lies in its compatibility with conventional local anaesthetics.

Within the scope of the present invention, it is possible however to use any anaesthetic that can be administered by spinal administration, independently of its period of action.

For example, short-acting local anaesthetics such as lidocaine, articaine, oxybuprocaine, chloroprocaine, or a medium-acting local anaesthetic selected from prilocaine, mepivacaine, etidocaine, or a long-acting local anaesthetic selected from ropivacaine, bupivacaine, cinchocaine, levobupivacaine, proxymetacaine and tetracaine are used within the scope of the invention.

The present invention claims the priority of Italian patent application MI2012A001154 of 29 Jun. 2012, the content of which is fully incorporated herein by reference.

The present invention will now be described with reference to the following examples, which are provided purely for illustrative purposes and are not to be understood to limit the present invention.

Example 1

Acetaminophen supersaturated solution injectable by spinal administration having the following formulation:

| | |
|---|---|
| acetaminophen | 15 mg |
| injectable sterile water | 1 ml |

The solution had a pH of 5.7

Example 2

Acetaminophen supersaturated buffered solution injectable by spinal administration having the following formulation:

| | |
|---|---|
| acetaminophen | 20 mg |
| injectable sterile water | 1 ml |
| citric acid | 0.45 mg |
| sodium dihydrogen phosphate | 0.91 mg |

The pH of the solution was approximately 5.5

Example 3

Buffered acetaminophen supersaturated solution injectable by spinal administration having the following formulation:

| | |
|---|---|
| acetaminophen | 80 mg |
| injectable sterile water | 1 ml |
| citric acid | 0.45 mg |
| sodium dihydrogen phosphate | 0.91 mg |

The pH of the solution was approximately 5.5

Example 4

Combined anaesthetic-analgesic formulation injectable by spinal administration, having the following formulation:

| | |
|---|---|
| acetaminophen | 20 mg |
| chloroprocaine | 10 mg |
| injectable sterile water | 5 ml |

Example 5

3 acetaminophen solutions having different concentrations were studied:
unsaturated solution containing 10 mg/ml (1.0%) of acetaminophen,
supersaturated solution containing 15 mg/ml (1.5%) of acetaminophen supersaturated solution containing 20 mg/ml (2.0%) of acetaminophen
hypersaturated solution containing 25 mg/ml (2.5%)
and two formulations: acetaminophen in water and acetaminophen in water+citrate buffer.

The acetaminophen solutions were prepared using water deoxygenated by means of nitrogen flushing (oxygen residue<200 ppb); in the case of the solutions of acetaminophen alone, initial pH values around 6.0 were obtained independently of the concentration of the acetaminophen itself, in any case ranging between 4.5 and 6.5.

The active ingredient was solubilised in heated water in defined conditions (approximately 50° C.). The solution thus obtained can be stored in the long term within a wide range of temperatures without reprecipitation and/or chemical alteration of the acetaminophen.

The solubility of the acetaminophen at 20° C. was approximately 13 mg/ml (1.3% w/v).

The acetaminophen solutions were obtained by means of a process requiring the following schematic steps:
a) dissolution in water deoxygenated by means of degassing in nitrogen flow of the active ingredient and of the excipients for the formulations where present
b) filtration of the solution in nitrogen stream
c) distribution of the solution in nitrogen stream
d) sterilisation of the vials at 121° C. for 15 minutes.

The following injectable solutions were obtained:

| mg/ml | RD029 natural pH | RD029 buffered pH | RD028 natural pH | RD028 buffered pH | RD026 natural pH | RD026 buffered pH |
|---|---|---|---|---|---|---|
| Acetaminophen | 10 | 10 | 15 | 15 | 20 | 20 |
| Citric acid | — | 0.45 | — | 0.45 | — | 0.45 |
| Disodium phosphate | — | 0.91 | — | 0.91 | — | 0.91 |
| WFI | 990 | 988.64 | 985 | 983.64 | 980 | 978.64 |

Once charged into the dissolver, the water for injection was degassed by means of boiling and was then cooled to 60° C. Acetaminophen and, for the buffered solutions, citric acid and disodium phosphate was/were added. The solution was left under stirring, maintaining a constant influx of nitrogen, for 25 minutes.

The pH value measured at this point of the preparation process revealed the following results:

| | RD029 natural pH | RD029 buffered pH | RD028 natural pH | RD028 buffered pH | RD026 natural pH | RD026 buffered pH |
|---|---|---|---|---|---|---|
| pH | 5.39 | 5.72 | 5.42 | 5.76 | 4.89 | 5.82 |

After 25 minutes from the addition of active ingredient and excipients and reaching 40° C., the solution was then filtered under nitrogen pressure and was collected in flasks previously purged with inert gas ($N_2$). The solution was distributed into vials in nitrogen stream, and the vials were subjected to final sterilisation in autoclave in overkill conditions (121° C. for 15 minutes).

The analyses carried out on the vials after sterilisation provided the following results:

| | RD029 natural pH | RD029 buffered pH | RD028 natural pH | RD028 buffered pH | RD026 natural pH | RD026 buffered pH |
|---|---|---|---|---|---|---|
| Colour and transparency | compliance | compliance | compliance | compliance | compliance | compliance |
| pH of the solution | 5.9 | 5.8 | 5.9 | 5.8 | 6.0 | 5.8 |
| Acetaminophen titre (HPLC) | 100.5 | 100.9 | 101.4% | 101.0% | 100.2% | 100.6% |
| 4-anminophenol (HPLC) | not observed | not observed | not observed | not observed | not observed | not observed |
| Diacetaminophen titre (HPLC) | not observed | not observed | not observed | not observed | not observed | not observed |
| Titre of other impurities (HPLC) | not observed | not observed | not observed | not observed | not observed | not observed |
| Particulate contamination | ≥10 µm 5.20; ≥25 µm 0.33 | ≥10 µm 12.67; ≥25 µm 0.33 | ≥10 µm 7.87; ≥25 µm 0.67 | ≥10 µm 7.47; ≥25 µm 0.13 | ≥10 µm; 8.74; ≥25 µm 0.21 | ≥10 µm 9.41; ≥25 µm; 0.32 |

Stability of the Acetaminophen Solutions Studied

Stability: 3 batches with respective acetaminophen concentration of 1%, 1.5% and 2% w/v were placed at 4° C., 25° C., 30° C., 40° C. and 60° C.

Chemical-physical analyses were not conducted on the samples at 4° C. The objective of the storage at low temperatures was to confirm any recrystallisation of the active ingredient. To this end, the samples were subjected to weekly visual analyses. After 3 months, the presence of precipitate was not found in any of the tested solutions.

After 9 months at 25 and 30° C., 6 months at 40° C., and 3 months at 60° C., the solutions were unchanged from a chemical-physical viewpoint.

The pH of the unbuffered solutions demonstrates a rising trend, starting from values from approximately 6.0 and reaching 6.5 under the condition of maximum stress (60° C.).

The acetaminophen titre remains unchanged. The product of oxidation, 4-aminophenol, always remains below the detection limit of the HPLC method used for the analyses. The concentration of the dimer always remains less than 0.10%. No other impurities are observed.

Example 6

5 solutions of acetaminophen with different concentrations were analyzed
supersaturated solution with acetaminophen content of 20 mg/ml (2.0%), 5 ml vials filled to 3 ml supersaturated solution with acetaminophen content of 25 mg/ml (2.5%), 5 ml vials filled to 3 ml
supersaturated solution with acetaminophen content of 30 mg/ml (3.0%), 5 ml vials filled to 3 ml
supersaturated solution with acetaminophen content of 50 mg/ml (5.0%), 5 ml vials filled to 3 ml
supersaturated solution with acetaminophen content of 80 mg/ml (8.0%), 5 ml vials filled to 3 ml The acetaminophen solutions were prepared using water deoxygenated by nitration (residual oxygen<200 ppb). Initial pH values of around 5.5 were obtained, regardless of the concentration of the acetaminophen itself, in each case of between 4.5 and 6.5. The solubilization of the active ingredient took place in water for injection maintained at a temperature of between 55 and 70° C. The solution thus obtained can be stored at length under these temperature conditions without precipitation and/or chemical alteration of the acetaminophen.

The acetaminophen solutions were obtained with a process that provided for the following schematic steps:
a) Dissolution in deoxygenated water by degassing of the active ingredient in a nitrogen flow at a temperature range from 55 and 70° C.
b) Filtration of the solution in a nitrogen stream at a temperature range from 70 to 80° C.
c) Distribution of the solution in a nitrogen stream at a temperature range from 55 to 75° C.
d) Sterilization of the vials at 121° C. for 15 minutes.

The following injectable solutions were produced:

| mg/ml | RD036 | RD037 | RD039 | RD040 | RD042 |
|---|---|---|---|---|---|
| Acetaminophen | 20 | 25 | 30 | 50 | 80 |
| WFI | 980 | 975 | 970 | 950 | 920 |

After loading in the dissolver, the water for injections was degassed by boiling and then cooled to 70° C. Acetaminophen was added. The solution was left under stirring, while maintaining a constant influx of nitrogen and the temperature above 55° C. for 25 minutes.

The pH value measured around 55° C. and at this point of the preparation gave the following results:

|  | RD036 | RD037 | RD039 | RD040 | RD042 |
|---|---|---|---|---|---|
| pH | 5.49 | 5.48 | 5.40 | 5.25 | 5.10 |

25 minutes after adding the active ingredient, the solution was brought to 80° C., filtered under nitrogen pressure and collected in flasks in previously purged with an inert gas ($N_2$). The distribution into vials took place in a nitrogen stream and the vials were subjected to terminal sterilization in an autoclave under over-kill conditions (121° C. for 15 minutes).

The analysis carried out on the vials following sterilization gave the following results:

|  | RD036 | RD037 | RD039 | RD040 | RD042 |
|---|---|---|---|---|---|
| Colour and transparency | Compliant | Compliant | Compliant | Compliant | Compliant |
| pH of the solution | 6.2 | 6.2 | 6.0 | 5.8 | 5.8 |
| Acetaminophen titre (HPLC) | 100.5% | 101.4% | 101.3% | 101.8% | 100.9% |
| 4-aminophenol titre (HPLC) | Not detected | Not detected | Not detected | Not detected | Not detected |
| Di-acetaminophen titre (HPLC) | Not detected | Not detected | Not detected | Not detected | Not detected |
| Titre of other impurities (HPLC) | <0.05%* | <0.05%* | <0.05%* | <0.05%* | <0.05%* |
| Particulate contamination | ≥1 μm: 733.40 ≥25 μm: 9.80 | ≥10 μm: 32.20 ≥25 μm: 11.80 | ≥10 μm: 311.20 ≥25 μm: 196.20 | ≥10 μm: 3.80 ≥25 μm: 0.20 | ≥10 μm: 20.10 ≥25 μm: 5.80 |

*disregard limit

Stability of the Acetaminophen Solutions Studied

Stability: 5 batches with acetaminophen concentration of 2.0%, 2.5%, 3%, 5% and 8% w/v respectively were placed at 4° C., 25° C. and 40° C.;

Physicochemical analyses were not conducted on the samples at 4° C. The purpose of storage at low temperatures was to check any recrystallization of the active ingredient. For this purpose, the samples were subjected to weekly visual analysis. After 2 months, there was no evidence of the presence of precipitate in the tested solutions.

After 2 months at 25, 40 and 4° C., the solutions are unchanged from a physicochemical perspective.

The pH of the solutions show an increasing trend starting from values of about 5.5 and reaching 6.0 in the condition of maximum stress (40° C.).

The titre of the acetaminophen remains unchanged. They 4-aminophenol impurity always remains below the detection limit of the HPLC method used for the analysis. The concentration of the dimer is always less than 0.1%. No other impurities were detected.

Example 7

Chemical-Physical Stability of the Mixtures of Acetaminophen and Local Anaesthetics for Spinal Use The solutions with a concentration of acetaminophen of 1.5% and 2% w/v of example 5 were mixed with various anaesthetics for spinal use (from the classes of amides and esters, for example bupivacaine HCl, lidocaine HCl, prilocaine HCl, chloroprocaine HCl, mepivacaine HCl, ropivacaine HCl) in various proportions so as to cover the entire known dosage range of each of these anaesthetics and a dosage range of acetaminophen from 10 mg to 60 mg.

Such mixtures were prepared using equipment and methodologies commonly used by anaesthetists (syringes, needles and orders of addition of the components).

The tests carried out involved the following anaesthetics for spinal use:
chloroprocaine 1%: minimum dosage: 4 ml; maximum dosage 5 ml
chloroprocaine 3%: minimum dosage: 1.3 ml; maximum dosage 1.7 ml
hyperbaric prilocaine 2%: minimum dosage: 2 ml; maximum dosage 3 ml
prilocaine 2%: minimum dosage: 2.5 ml; maximum dosage 4 ml
ropivacaine 5 mg/ml: minimum dosage: 3 ml; maximum dosage 5 ml ropivacaine 10 mg/ml: minimum dosage: 1.5 ml; maximum dosage 2.5 ml
hyperbaric bupivacaine 0.5%: minimum dosage: 1.5 ml; maximum dosage 4 ml
mepivacaine 2%: minimum dosage: 1 ml; maximum dosage 3 ml
mepivacaine 4%: minimum dosage: 0.5 ml; maximum dosage 1.5 ml
lidocaine 0.5%: minimum dosage: 8 ml; maximum dosage 16 ml
lidocaine 2%: minimum dosage: 2 ml; maximum dosage 4 ml Mixtures with the solutions of acetaminophen 1.5% and 2% with dosages from 10 mg to 60 mg were prepared for each dosage, both minimum and maximum, of each anaesthetic for spinal use:

acetaminophen 1.5%: minimum dosage: 0.7 ml; maximum dosage 4 ml
acetaminophen 2%: minimum dosage: 0.5 ml; maximum dosage 3 ml The two products (anaesthetic and acetaminophen) were mixed in accordance with the operative procedures commonly used in the field of anaesthesia. The solutions were drawn using the same sterile syringe through a needle of 18G diameter and by dispensing the mixture thus created into a glass vial using a needle for spinal anaesthesia (the diameters used were 24G, 25G, and 27G).

The order in which the solutions were drawn (first anaesthetic and then acetaminophen and vice versa) was varied a number of times in order to assess both the records and the resultant mixtures, which were monitored for 10 days in order to assess the absence of precipitate.

None of the prepared solutions demonstrated the presence of precipitate up to 10 days from preparation.

The mixture with minimum dosage of hyperbaric bupivacaine 0.5% (1.5 ml) and maximum dosage of acetaminophen 2% (3 ml) was prepared 3 times. The first time in accordance with the usual operative procedures, the second time leaving the mixture in the syringe and placing it at a temperature of 4° C. for 10 days, and the third time preparing the mixture at a temperature of 15° C. In none of these cases was the presence of crystals and/or precipitate observed.

Two tests without addition of anaesthetic, but only with drawing of acetaminophen 2% were also carried out. In the first test, the acetaminophen was drawn via syringe through an 18G needle and was dispensed into a glass vial through a 27G needle. One hour after dispensing of the solution, there was no sign of the presence of crystals and/or precipitate; 19 hours after preparation, the presence of needle-shaped crystals was observed.

In the second test, acetaminophen 2% was drawn via syringe through an 18G needle and was left in the syringe. The formation of crystals within the solution was observed after 30 minutes.

All of the mixtures thus produced were analysed from a chemical view point both with regard to the acetaminophen and with regard to the active ingredient of the anaesthetic. No significant instances of degradation were observed in any case within 24 hours.

Example 8

The efficacy of the acetaminophen supersaturated solution administered by spinal administration (IT) was tested by means of explorative experiments in a model of inflammatory pain in mice, induced by means of intraplantar injection (injection in the rear left paw, referred to hereinafter as the "site of inflammation") of carrageenan (50 µl 1%).

The pain threshold following mechanical stimulation (expressed in grams) was measured after 2, 4, 6 and 24 hours after induction of the inflammation. This threshold is to be considered an indicator of inflammatory pain.

The development of oedema at the site of inflammation was measured and expressed as an increase of volume (mL) of the site of inflammation.

Spinal administration in the mouse was carried out as described by Fairbanks (2003).

Experimental Groups:
N=5 mice received spinal vehicle (IT; to be understood as a placebo) and intraplantar administration of carrageenan
N=7 mice received acetaminophen IT (10 µg) and intraplantar administration of carrageenan
N=7 mice received acetaminophen IT (100 µg) and intraplantar administration of carrageenan Results IT acetaminophen in the dose of 100 µg per mouse was effective in reducing inflammatory pain in the mouse. The mice to which IT acetaminophen was administered in the dose of 100 µg had a significantly higher pain threshold following mechanical stimulation of the site of inflammation (FIG. 1).

Figure 2:
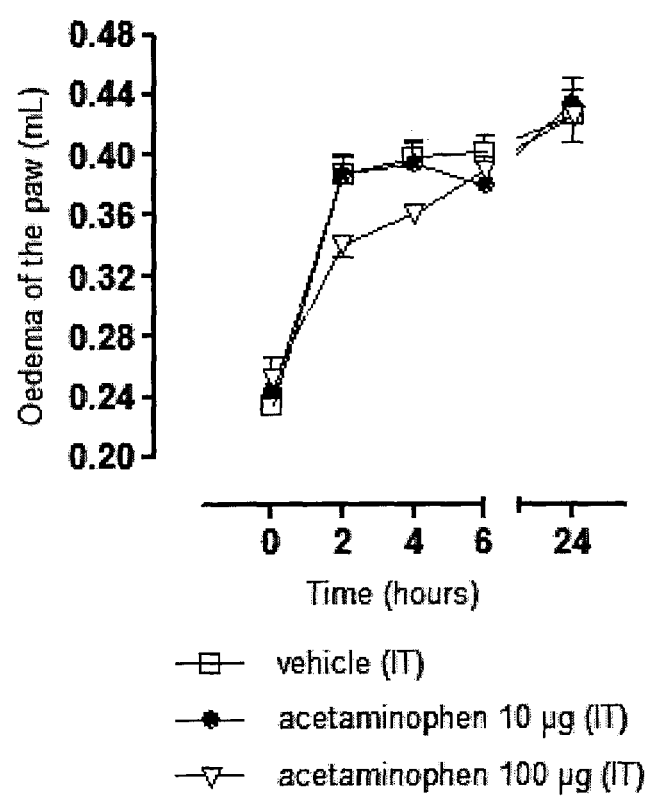
FIG. 2 shows a graph illustrating the development of oedema resulting from peripheral inflammation measured as an increase in the volume of the paw of laboratory mice.

IT acetaminophen in the dose of 100 µg per mouse produced only a slight reduction (approximately 20%) of the development of oedema at the site of inflammation during the first two hours following induction (FIG. 2).

IT acetaminophen in the dose of 10 µg per mouse was not effective in reducing the inflammatory pain insignificantly compared to the group of control mice (FIG. 1).

At all tested doses, IT acetaminophen did not produce any clear sign of toxicity or clear behavioural and motor changes.

The accompanying FIG. 1 shows the pain threshold following mechanical stimulation at the site of inflammation after IT administration of placebo, 10 µg of acetaminophen and 100 µg of acetaminophen.

FIG. 2 shows the development of oedema at the site of inflammation during the first two hours after induction after IT administration of placebo, 10 µg of acetaminophen and 100 µg of acetaminophen. The raw data and the relative statistical analysis of example 6 will be presented hereinafter.

Threshold of Mechanical Hyperalgesia (Values Expressed in Grams)

| Vehicle | | | | | | |
|---|---|---|---|---|---|---|
| basal | 42.5 | 32.5 | 47.5 | 37.5 | 32.5 | |
| 2 hours | 13 | 14 | 9 | 9 | 8 | |
| 4 hours | 12 | 13 | 8.5 | 9 | 9 | |
| 6 hours | 11.5 | 10 | 9.5 | 11 | 9 | |
| 24 hours | 12 | 10.5 | 8 | 8.5 | 7.5 | |

| Acetaminophen 10 µg | | | | | | |
|---|---|---|---|---|---|---|
| basal | 32.5 | 42.5 | 32.5 | 32.5 | 22.5 | 30.0 | 25.0 |
| 2 hours | 8.0 | 9.0 | 11.5 | 8.0 | 8.0 | 9.0 | 10.0 |
| 4 hours | 13.0 | 7.0 | 7.5 | 13.0 | 9.0 | 7.0 | 8.5 |
| 6 hours | 11.5 | 13.0 | 9.0 | 11.0 | 10.0 | 7.5 | 10.0 |
| 24 hours | 13.0 | 11.5 | 12.0 | 13.0 | 12.0 | 9.5 | 11.5 |

| Acetaminophen 100 µg | | | | | | |
|---|---|---|---|---|---|---|
| basal | 27.5 | 35 | 20 | 37.5 | 32.5 | 30 | 30 |
| 2 hours | 23.5 | 12.5 | 23 | 17 | 13.5 | 14 | 11.5 |
| 4 hours | 20 | 17.5 | 20 | 16 | 20 | 17.5 | 15 |
| 6 hours | 20 | 15 | 21.5 | 15.5 | 16 | 17 | 16 |
| 24 hours | 19 | 14.5 | 19 | 21.5 | 16.5 | 18 | 17 |

Paw Volume (Oedema) (Values Expressed in mL)

| Vehicle | | | | | |
|---|---|---|---|---|---|
| basal | 0.25 | 0.25 | 0.23 | 0.2 | 0.24 |
| 2 hours | 0.4 | 0.41 | 0.39 | 0.35 | 0.39 |
| 4 hours | 0.42 | 0.42 | 0.39 | 0.39 | 0.37 |
| 6 hours | 0.41 | 0.44 | 0.4 | 0.39 | 0.37 |
| 24 hours | 0.48 | 0.44 | 0.43 | 0.38 | 0.4 |

| Acetaminophen 10 µg | | | | | | |
|---|---|---|---|---|---|---|
| basal | 0.29 | 0.24 | 0.2 | 0.21 | 0.26 | 0.22 | 0.29 |
| 2 hours | 0.43 | 0.36 | 0.38 | 0.37 | 0.44 | 0.36 | 0.37 |
| 4 hours | 0.39 | 0.36 | 0.34 | 0.38 | 0.44 | 0.41 | 0.44 |
| 6 hours | 0.44 | 0.38 | 0.33 | 0.37 | 0.45 | 0.33 | 0.36 |
| 24 hours | 0.47 | 0.4 | 0.46 | 0.37 | 0.5 | 0.42 | 0.42 |

| Acetaminophen 100 µg | | | | | | |
|---|---|---|---|---|---|---|
| basal | 0.27 | 0.28 | 0.29 | 0.24 | 0.26 | 0.25 | 0.18 |
| 2 hours | 0.32 | 0.34 | 0.33 | 0.33 | 0.37 | 0.36 | 0.33 |
| 4 hours | 0.35 | 0.37 | 0.38 | 0.36 | 0.38 | 0.35 | 0.34 |
| 6 hours | 0.38 | 0.4 | 0.39 | 0.38 | 0.43 | 0.4 | 0.35 |
| 24 hours | 0.33 | 0.41 | 0.42 | 0.44 | 0.47 | 0.45 | 0.46 | each column represents a different experimental subject

Example 9

The efficacy of the acetaminophen supersaturated solution administered by spinal administration (IT) was tested with explorative experiments in a model of post-surgical pain in rats. The post-surgical pain was induced by means of incision and subsequent suture of the subplantar region of the rear left paw, as described by Timothy J. Brennan (1996).

The pain threshold following mechanical stimulation (expressed in grams) was measured after 2, 4, 6 and 24 hours after the incision. This threshold is considered to be an indicator of pain and hyperalgesia of the zone affected by surgical intervention.

Experimental Groups

N=5 rats received spinal vehicle (IT; to be understood as placebo) immediately before the surgical procedure.

N=5 rats received acetaminophen IT (200 µg) immediately before the surgical procedure.

Results

Figure 3:
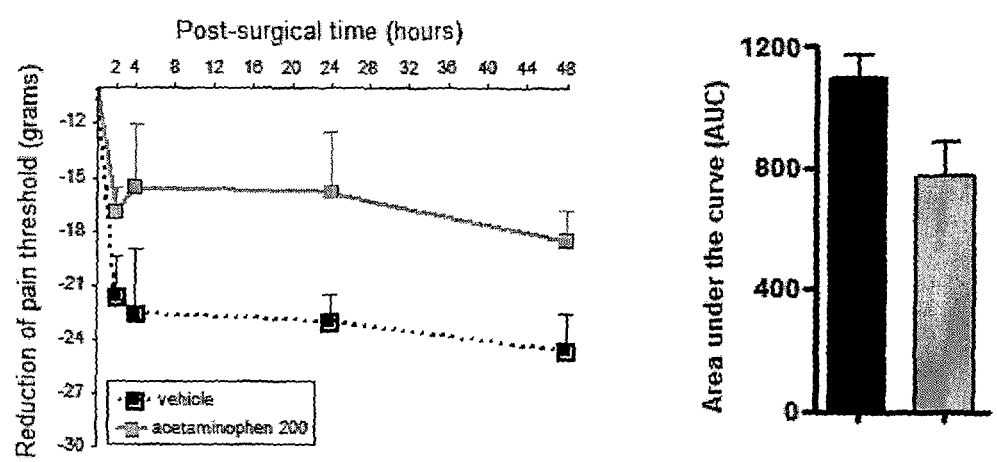
FIG. 3 shows a graph illustrating the analgesic effect over time of a solution containing 200 μg of acetaminophen in a model of post-surgical pain in rats.

IT acetaminophen in the dose of 200 µg per rat was effective in reducing post-surgical pain, as shown in FIG. 3. The rats to which IT acetaminophen was administered in the dose of 200 µg had a significantly higher pain threshold following mechanical stimulation of the site of incision (FIG. 3). IT acetaminophen in the dose of 200 µg produced significant cumulative analgesia over 24 hours.

IT acetaminophen did not produce any clear sign of toxicity or clear behavioural or motor changes. The raw data and the relative statistical analysis according to the present example will be presented hereinafter.

| Raw data pain threshold | | | | | | | | | | |
|---|---|---|---|---|---|---|---|---|---|---|
| TIME | | | VEHICLE | | | | | ACETAMINOPHEN 200 | | |
| 0 | 48.25 | 46.75 | 39.5 | 44.25 | 45.25 | 45 | 45 | 41 | 42.25 | 41.5 |
| 2 | 18.25 | 24.5 | 20.75 | 25 | 27.25 | 27 | 23.5 | 27.75 | 27 | 25 |
| 4 | 20.25 | 17 | 28.75 | 17.75 | 27.25 | 22.75 | 23.5 | 24 | 28 | 38.75 |
| 24 | 25.8 | 18.5 | 20.5 | 22.5 | 21.5 | 29.25 | 18.25 | 29 | 24.5 | 34.75 |
| 48 | 17.25 | 24.75 | 18.5 | 23.25 | 17 | 22.25 | 29 | 26.25 | 9.76 | 24.75 |

| Absolute reduction of the pain threshold | | | | | | | | | | |
|---|---|---|---|---|---|---|---|---|---|---|
| TIME | | | | | | | | | | |
| 2 | −30 | −22.25 | −18.75 | −19.25 | −18 | −18 | −21.5 | −13.25 | −15.25 | −16.5 |
| 4 | −28 | −29.75 | −10.75 | −26.5 | −18 | −22.25 | −21.5 | −17 | −14.25 | −2.75 |
| 24 | −22.45 | −28.25 | −19 | −21.75 | −23.75 | −15.75 | −26.75 | −12 | −17.75 | −6.75 |
| 48 | −31 | −22 | −21 | −21 | −28.25 | −22.75 | −16 | −14.75 | −22.49 | −16.75 |

| Reduction of the pain threshold in % | | | | | | | | | | |
|---|---|---|---|---|---|---|---|---|---|---|
| TIME | | | | | | | | | | |
| 2 | 37.82 | 52.41 | 52.53 | 56.50 | 60.22 | 60.00 | 52.22 | 67.68 | 63.91 | 60.24 |
| 4 | 41.97 | 36.36 | 72.78 | 40.11 | 60.22 | 50.56 | 52.22 | 58.54 | 66.27 | 93.37 |
| 24 | 53.47 | 39.57 | 51.90 | 50.85 | 47.51 | 65.00 | 40.56 | 70.73 | 57.99 | 83.73 |
| 48 | 35.75 | 52.94 | 46.84 | 52.54 | 37.57 | 49.44 | 64.44 | 64.02 | 46.77 | 59.64 |

Example 10

The efficacy of the acetaminophen supersaturated solution administered by spinal administration (IT) was tested with explorative experiments in a model of post-surgical pain in rats in combination with a solution of chloroprocaine 3%.

The post-surgical pain was induced by means of incision and subsequent suture of the subplantar region of the rear left paw, as described by Timothy J. Brennan (1996).

The pain threshold following mechanical stimulation (expressed in grams) was measured 4 hours after the incision. Complete reduction of the anaesthetic effect of the spinal chloroprocaine is expected within this period of time. The reduction of the pain threshold is considered to be an indicator of pain and hyperalgesia of the zone affected by surgical intervention.

Experimental Groups

N=5 rats received spinal vehicle (IT; to be understood as placebo) immediately before the surgical procedure N=5 rats received acetaminophen IT (200 µg) immediately before the surgical procedure N=4 rats received chloroprocaine IT (3%, 20 µL) immediately before the surgical procedure N=4 rats received acetaminophen IT (200 µg)+chloroprocaine IT (3%, 20 µL) immediately before the surgical procedure.

Results

Figure 4:
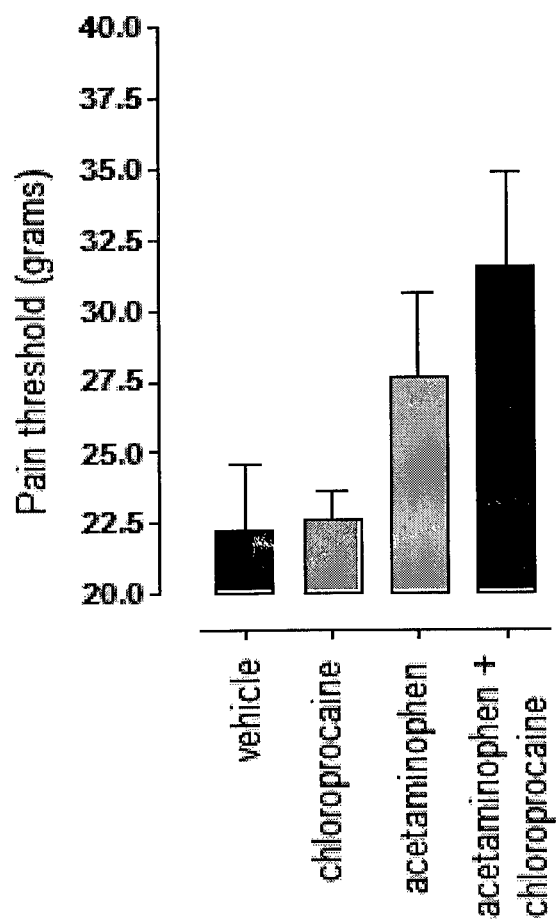
FIG. 4 shows the effect of co-administration of acetaminophen (200 μg) and a solution of 3% chloroprocaine (20 μL)

IT acetaminophen in the dose of 200 µg per rat was effective in reducing post-surgical pain, as shown in FIG. 4. The rats to which IT acetaminophen was administered in the dose of 200 µg had a significantly higher pain threshold following mechanical stimulation of the site of incision (FIG. 4).

IT chloroprocaine (3%, 20 µL) for rats did not change the pain threshold following mechanical stimulation of the site of incision, indicating a termination of the anaesthetic effect.

IT acetaminophen in the dose of 200 µg for rats in co-administration with chloroprocaine (3%, 20 µL) produced a significant rise of the pain threshold following mechanical stimulation of the site of incision with a trend suggestive of an additional analgesic effect.

IT acetaminophen in the dose of 200 µg per rat in co-administration with chloroprocaine (3%, 20 µL) did not produce any clear sign of toxicity or clear behavioural or motor changes. The rats that received chloroprocaine (3%, 20 µL) had, after 4 hours, a complete recovery in terms of walking and tension of the rear limbs.

The raw data in accordance with the present example will be presented hereinafter.

| Rat no. | Vehicle | Chloroprocaine | Acetaminophen | Acetaminophen + Chloroprocaine |
|---|---|---|---|---|
| 1 | 20.25 | 23.60 | 22.75 | 37.00 |
| 2 | 17.00 | 22.75 | 24.90 | 28.75 |
| 3 | 28.75 | 19.75 | 24.00 | 37.00 |
| 4 | 17.75 | 24.25 | 28.00 | 23.50 |
| 5 | 27.25 |  | 38.75 |  |

The invention claimed is:

1. A stable, single unit dose formulation of a supersaturated acetaminophen aqueous solution, said formulation consisting of:
    acetaminophen and water, wherein the concentration of acetaminophen is 2% w/v to 5% w/v in a volume of 1 mL to 5 mL of a water, and
    wherein the formulation has less than 200 ppb of air or oxygen dissolved in the water.

2. A stable, single unit dose formulation of supersaturated acetaminophen consisting of:
    acetaminophen,
    water, and
    a local anaesthetic, wherein the concentration of acetaminophen is 2% w/v to 5% w/v and total volume of the formulation is between 1 mL and 6 mL, and
    wherein the formulation has less than 200 ppb of air or oxygen dissolved in the water.

3. The stable, single unit dose formulation of supersaturated acetaminophen of claim 2, wherein the local anaesthetic is a short-acting local anaesthetic selected from lidocaine, articaine, oxybuprocaine, and chloroprocaine or a medium-acting local anesthetic selected from prilocaine, mepivacaine, and etidocaine.

4. The stable, single unit dose formulation of supersaturated acetaminophen of claim 2, wherein the local anaesthetic is long-acting local anaesthetic selected from ropivacaine, bupivacaine, cinchocaine, levobupivacaine, proxymetacaine, and tetracaine.

* * * * *